US00PP16293P3

(12) United States Plant Patent
Orton et al.

(10) Patent No.: US PP16,293 P3
(45) Date of Patent: Feb. 28, 2006

(54) **INTERSPECIFIC *CORNUS* HYBRID DESIGNATED KN4-43**

(50) Latin Name: ***Cornus kousa*×*C. nuttallii***
Varietal Denomination: KN4-43

(75) Inventors: Elwin R. Orton, Hillsborough, NJ (US); David A. Gant, Wall Township, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 10/741,618

(22) Filed: Dec. 19, 2003

(65) Prior Publication Data

US 2005/0138706 P1 Jun. 23, 2005

(51) Int. Cl.
*A01H 5/00* (2006.01)

(52) U.S. Cl. ..... Plt./220
(58) Field of Classification Search ..... Plt./220
See application file for complete search history.

(56) References Cited

U.S. PATENT DOCUMENTS

PP13,384 P3 * 12/2002 Lipka ..... Plt./220
PP14,537 P3 * 2/2004 Elsley ..... Plt./220

OTHER PUBLICATIONS http://www.landsteward.com/page.cfm/10331?template=Plant.*
TESS Venus US Trademark Application Serial No. 76556303.*

* cited by examiner

*Primary Examiner*—Kent Bell
*Assistant Examiner*—W. C. Haas
(74) *Attorney, Agent, or Firm*—James A. Lucas; Driggs, Lucas, Brubaker & Hogg Co., LPA

(57) ABSTRACT

An interspecific hybrid of *Cornus kousa*×*C. nuttallii* exhibits the vigorous nature and the floral display of large, white bracts of plants of *C. nuttallii* and the dark, glossy green foliage and disease and insect resistance of plants of *C. kousa.* The hybrid thus provides a new, unique, and superior large-bracted dogwood for landscaping purposes. Plants of *C. nuttallii* become very large in nature in areas where they are indigenous but seldom thrive in other areas. Plants of this novel hybrid are expected to thrive in many regions of the world where plants of *C. kousa* perform well.

2 Drawing Sheets

Botanical description: Botanic name: $F_1$ interspecific hybrid of *Cornus kousa*×*C. nuttallii.*
Variety denomination: 'KN4-43'.

BACKGROUND OF THE INVENTION

This new cultivar is the product of a long standing detailed program of interspecific hybridization and selection of dogwoods, in this instance from hybrid seedlings of *Cornus kousa* an ornamental Asiatic dogwood and *Cornus nuttallii,* a giant, large bracted dogwood that is indigenous to the Pacific Northwest of North America. Records of these hybrids were carefully retained and characteristics analyzed for their differences and outstanding value as potential commercial varieties or cultivars.

We have selected the particular seedling hereof from certain progeny grown in a cultivated area and, as a result, have in turn caused the same to be asexually reproduced by grafting (usually T-budding or chip budding). It also can be propagated by softwood cuttings. The reproduction and actual growth and selection of the new cultivar took place in the vicinity of New Brunswick, N.J. and has been found to be distinctive as to its vegetative winter-hardiness in that area, USDA Plant Hardiness Map Zone 6a.

As will be understood from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore suggested.

SUMMARY OF THE INVENTION

The variety was originated or discovered on Horticulture Farm No. 1 of New Jersey Agricultural Experiment Station, Ryders Lane at US Route 1, New Brunswick, N.J. 08901, Middlesex County. This single seedling resulted from a controlled cross successfully accomplished on May 4, 1973. The seedling which became this new variety germinated Apr. 15, 1974, was field planted Mar. 17, 1975, as Plant 22 in Row 52 of research field No. 22 and is still at this location as a thirty-year-old plant. The seed parent is *Cornus kousa* (Buerger ex. Miq.) Hance 'Simpson No. 1' (Non-patented). The pollen parent is *Cornus nuttallii* Aud. 'Goldspot' (Non-patented). Reproduction took place on Horticulture Farm No. 1, Rutgers University, New Brunswick, N.J. It has also been propagated by nurserymen in Tennessee, Oregon, and California under formal testing agreement with the NJAES, Cook College/Rutgers University. To the best of our knowledge, this new variety is the first reported $F_1$ interspecific hybrid involving plants of these two species.

BRIEF DESCRIPTION OF THE DRAWINGS

This new cultivar of dogwood is illustrated by the accompanying photographic drawings, depicting the plant by the best possible color representation using color photography. All color references below are measured against The Royal Horticultural Society (R.H.S.) Colour Chart. Colors are approximate as color depends on horticultural practices, such as light level and fertilization rate, among others.

BOTANICAL DESCRIPTION OF THE INVENTION

Figure 1:
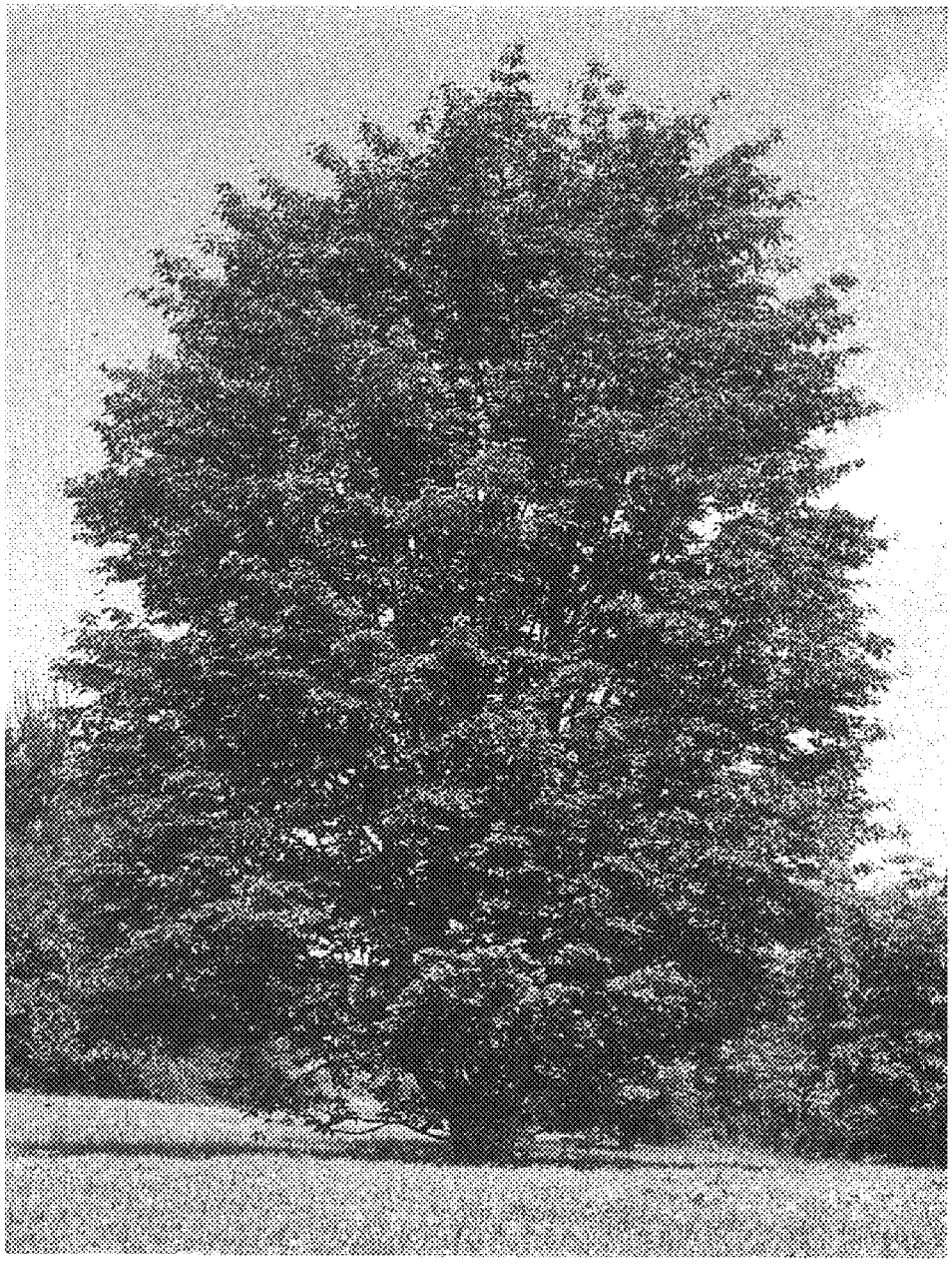
FIG. 1 shows the original dogwood tree of the present invention after 30 growing seasons.
Figure 2:
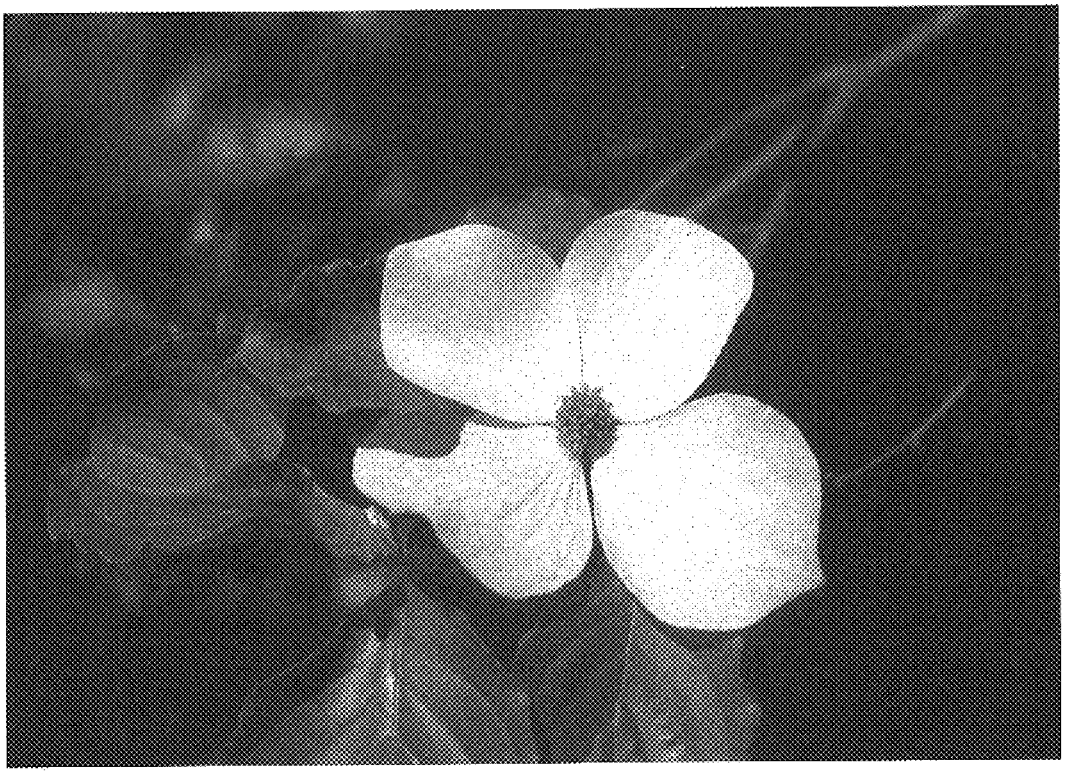
FIG. 2 shows a single flower head of the tree shown in FIG. 1 taken at the time of floral display, and indicates the color and shape of the floral bracts.

Plant:
Form: Tree.
Growth habit: Erect and uniformly wide.
Growth: Very vigorous; densely branched and foliaged.
Height: 8.83 m tall at 30 years.
Spread: 7.07 m in diameter at 30 years.
Plant vigor: This new interspecific $F_1$ hybrid is less vigorous than the *C. nuttalii* parent as plants of *C. nuttallii* are the giants of the large-bracted dogwoods, reaching 24 meters in nature in the Pacific Northwest of North America where the plants are indigenous. However, plants of this hybrid are at least 100% more vigorous than typical plants of *C. kousa*. One-year liners of this hybrid propagated in Oregon by budding are nearly twice the size of one-year liners of *C. kousa* as the hybrid liners typically are 1.2 m in height and are very stout.
Cold hardiness: Plants are vegetatively hardy in USDA Plant Hardiness Map Zone 6a (−5° to −10° F.) but the floral display of the involucral bracts is very poor as development of the bracts is arrested due to winter-kill of many flowers of the inflorescence. Plants exhibit good floral display in areas of Plant Hardiness Map Zone 7a (+5° to 0° F.). Plants are subject to "bark-split" on the south and/or west sides of the tree trunk on bright, sunny days during January in USDA Plant Hardiness Map Zone 6a.
Resistance to insects and disease: No insect or disease problems have been observed during the twenty-eight years the original $F_1$ interspecific hybrid seedling has been tested in the field.
Truck: Circumference of the crown of the original seedling at the soil level, below the three upright trunks, was 1.57 m at 30 years.
*Color.*—A mottle of spots of 197C and 197D (Greyed-Green Group).
*Texture.*—Sandpaper rough, bark exfoliating on lowest 3 to 4 feet. Color of trunk under exfoliating bark: a mottle of spots 166D (Greyed-Orange Group) and spots of 174B and/or spots of 174C (Greyed Orange Group).
Branches:
*Color.*—A mottle of Brown Group 200B and 197B, 198D Greyed-Green Group.
*Texture.*—Smooth, with tiny rough bumps (lenticels).
*Crotch angle.*—75°.
*Lenticels.*—Length: 1.25 m to 1.75 mm. Width: 0.4 mm to 0.65 mm. Color: closest to and/or in between 197A and 197B Greyed-Green Group. Number: abundant but density variable. Average (n=4) number of lenticels per $cm^2$ is 124.5.
Internode length.—5 cm to 7 cm.

Foliage:
Leaf arrangement: Opposite.
Leaf size.—Blade.

| Year | n | Average length (in cm) | n | Average width (in cm) |
|---|---|---|---|---|
| 2001 | 31 | 11.02 | 31 | 6.16 |
| 2002 | 30 | 10.33 | 30 | 5.92 |

Wherein 'n' as used throughout this description represents the number of measurements utilized to obtain the average measurements stated.

*Shape.*—Elliptic.
*Tip.*—Apiculate.
*Base.*—Obtuse.
*Margin.*—Entire.
Other features: Prominent midrib on abaxial surface, average of 5 to 6 secondary vein pairs; tufts of fine, whitish-tan pubescence at axils of midrib and secondary veins on abaxial surface of leaf. Interveinal areas of blade have scattered pubescence.
Quantity: Densely foliated.
Coloration: Solid.
Spring foliage color adaxial: 137A Green Group.
*Abaxial.*—137C Green Group.
Mature foliage color — Adaxial: 139A Green Group.
*Abaxial.*—137C Green Group.
Autumn foliage color (November): Of little ornamental value as about 70 percent of the leaves are nearly full green: 137A Green Group; the other leaves are 50 to 70 percent green (137A Green Group) with the remaining surface areas mottled with colors ranging from yellow (21B Yellow-Orange Group) to yellow and orange and red (21B Yellow-Orange Group; close to 46A Red Group but not as bright; 178A Greyed-Red Group) and red to burgundy (187A Greyed-Purple Group).
Texture:
*Adaxial side.*—Glossy, smooth.
*Abaxial side.*—Flat and smooth with prominent midrib.
Ribs and veins: Prominent midrib on abaxial surface.
Petiole: Color: 144A Yellow-Green Group (Spring and Summer); 144C (Autumn).
Stipules: Exstipulate.
Disease resistance: Not susceptible to powdery mildew or dogwood anthracnose in central New Jersey, in Boring, Oreg. or in Winchester, Tenn.
Inflorescence: Location where observations were made: Animal Research Farm, NJAES, North Brunswick, N.J.
Type of inflorescence: Flower head; Dense, rounded mound.

Average height and diameter of over-wintering flower buds is 8.7 mm and 6.25 mm (n=10), respectively.

Peduncle:

| Year | n | Average length (cm) | n | Average width (cm) |
|---|---|---|---|---|
| 1999 | 24 | 1.82 | 24 | 2.72 |
| 2001 | 25 | 1.77 | 19 | 3.24 |
| 2002 | 60 | 1.60 | 60 | 3.23 |
| 2003 | 33 | 1.48 | 33 | 3.14 |

The average peduncle length of this interspecific hybrid at the time of floral display is much shorter than that of its parent plants as the peduncle length for plants of *C. nuttallii* and *C. kousa* ranges from 3 cm to 8 cm and 5 cm to 10 cm, respectively. Color: 138C Green Group.

Vegetative bracts borne on peduncle: Two to three pair of opposing appressed bracts closely telescoped on the peduncle. Shape is that of an elongated isosceles triangle, the tips of the uppermost pair of bracts occasionally touch the basal pair of floral bracts at the base of the flower head.

Size of vegetative bracts: Variable, from 5 mm to 9 mm in length and 4 mm to 5 mm in width at base. Point of insertion on the peduncle is relatively far below the flower head, i.e., near the base of the peduncle.

Color of vegetative bracts: Closest to 145A Yellow-Green Group but 16A Greyed-Orange Group at the apex and along the margins of the bracts.

The vegetative bracts are similar to those of the *C. nuttallii* parent in being borne well below the flower head and do not enclose the true flowers in the overwintering floral buds. The bracts are dissimilar to those of the *C. kousa* parent as the upper set of vegetative bracts in plants of *C. kousa* completely enclose the true flowers in the overwintering flower buds.

Floral bracts:

Number: Typically four (in two pairs); infrequently 5 or 6.

Size: In cm, of upper floral bracts, as shown below:

| Year | n | Average length (cm) | Average width (cm) | Average Involucral Spread (cm) | n |
|---|---|---|---|---|---|
| 1999 | 50 | 5.01 | 3.96 | 10.30 | 25 |
| 2001 | 50 | 5.02 | 4.22 | 10.34 | 25 |
| 2002 | 60 | 5.30 | 4.78 | 10.90 | 30 |

Bract size will vary from year to year but the upper bracts will be longer and narrower than the lower bracts each year. The bract size of this new interspecific dogwood is within the size range typical for plants of *C. kousa* but is considerably smaller than the involucral spread of the *C. nuttallii* parent, *C.n.* 'Goldspot' which typically involves six floral bracts measuring 6 to 7.5 cm in length.

Color of floral bracts:

*Adaxial surface.*—Closest to 155A White Group but slightly more yellow.

*Abaxial surface.*—Closest to 155B White Group but slightly more yellow.

Shape of floral bracts: Broadly obovate.

*Apex of floral bracts.*—Abruptly acute.

*Base of floral bracts.*—Cuneate.

Flower description:

Flowering habit: Very floriferous. Single flowers arranged in compact, dense heads subtended by the large floral bracts. No observed fragrance. Flowers not persistent. Floral display of the bracts lasts about two to three weeks, depending on weather conditions.

Flowering habit: Anthesis of the tiny, relatively inconspicuous true flowers generally commences two to four days following the onset of the ornamental display of the large floral bracts which in New Brunswick, N.J. starts just as the floral display of plants of *C. florida* ceases, or about May $14^{th}$ in most years.

Number of true flowers per flower head:

| | | |
|---|---|---|
| 1999 | 75.00 | (n = 24) |
| 2001 | 77.24 | (n = 25) |
| 2002 | 77.30 | (n = 30) |
| 2003 | 78.70 | (n – 10) |

The number of true flowers per flower head of our interspecific hybrid is intermediate to that of the parent plants as the pistillate parent (*C. kousa*) has about 50 flowers per flower head and the staminate parent (*C. nuttallii*) typically has an average of 100 flowers per flower head.

Reproductive organs:

Stamens:

*Number.*—4.

*Color.*—Pale grayish-white.

*Filament.*—About 1.5 mm long and 0.25 mm wide.

*Anthers.*—Size: about 1 mm long and 0.25 mm wide.

*Pollen.*—Very sparse, white with hint of yellow.

Pistil:

*Number.*—1.

*Style.*—About 1.5 mm to 1.7 mm (including stigma 0.25 mm) long.

*Stigma.*—Approximately 0.4 mm in width.

*Color.*—Pale greenish-white.

Fruit:

Flower head with fruit: Round mound with flattened base. Exterior is rough as the single fruit are tightly compressed but separate and the style and sepals protrude at the apex of each fruit. Most fruit are parthenocarpic (without seed) as the plants are highly cross-sterile, as well as self-incompatible, and very few seeds develop.

The pericarp of the fruit is smooth and at maturity ranges from 34 Orange-Red Group to 42A Red Group and 44A Red Group, the fruit bearing a viable seed being the darkest in color.

A single fruit is about 1.0 cm long and 0.7 cm in width, ellipsoidal in shape and rather smooth if a well developed, viable seed is present, but the parthenocarpic fruit are smaller (shrunken) and rather angular (often 3 sided and somewhat flattened) in shape.

Seed color: Variable from 165E to 165C to 165D Greyed-Orange Group.

Seed: Size: Approximately 8 mm long and 4 mm to 5 mm wide.

What is claimed is:

1. A new and distinct cultivar of dogwood tree, substantially as herein shown and described, comprising an interspecific hybrid of *Cornus kousa*×*C. nuttallii*.

* * * * *